(12) United States Patent
Myshak et al.

(10) Patent No.: US 10,094,773 B2
(45) Date of Patent: Oct. 9, 2018

(54) APPARATUS AND METHOD FOR DETECTING A GAS USING AN UNMANNED AERIAL VEHICLE

(71) Applicant: ISIS GEOMATICS INC., Lethbridge (CA)

(72) Inventors: Stephen Myshak, Lethbridge (CA); Owen Brown, Lethbridge (CA)

(73) Assignee: ISIS GEOMATICS INC., Lethbridge (CA)

( * ) Notice: Subject to any disclaimer, the term of this patent is extended or adjusted under 35 U.S.C. 154(b) by 0 days.

(21) Appl. No.: 15/506,218

(22) PCT Filed: Aug. 24, 2015

(86) PCT No.: PCT/CA2015/050810
§ 371 (c)(1),
(2) Date: Feb. 23, 2017

(87) PCT Pub. No.: WO2016/029305
PCT Pub. Date: Mar. 3, 2016

(65) Prior Publication Data
US 2018/0209902 A1 Jul. 26, 2018

Related U.S. Application Data

(60) Provisional application No. 62/041,215, filed on Aug. 25, 2014.

(51) Int. Cl.
*G01N 21/25* (2006.01)
*G01N 21/39* (2006.01)
(Continued)

(52) U.S. Cl.
CPC ............ *G01N 21/39* (2013.01); *G01J 3/0202* (2013.01); *G01J 3/0208* (2013.01); *G01J 3/42* (2013.01);
(Continued)

(58) Field of Classification Search
CPC ... G01J 3/02; G01J 3/42; G01N 21/39; G01N 21/25; G01N 21/03; G01N 21/27; G01N 21/255; G01N 21/253; G01N 21/251
See application file for complete search history.

(56) References Cited

U.S. PATENT DOCUMENTS 7,411,196 B2   8/2008   Kalayeh
13,730,461     5/2014   Andreussi
(Continued)

FOREIGN PATENT DOCUMENTS

CA    2386268      5/2002
CN    203439256    2/2014
WO    2014026401   2/2014

OTHER PUBLICATIONS

International Search Report and Written Opinion, dated Nov. 23, 2015, received in International Application No. PCT/CA2015/050810.
(Continued)

*Primary Examiner* — Abdullahi Nur
(74) *Attorney, Agent, or Firm* — Davis Wright Tremaine, LLP; Heather M. Colburn

(57) ABSTRACT

A gas detection apparatus mountable to an unmanned aerial vehicle (UAV) comprises a transceiver module, a reflector module and an electronics module. The transceiver module comprises a laser emitter and a laser receiver; the laser emitter is tunable to emit a laser spectroscopy beam that can detect at least one target gas, and the laser receiver is configured to convert the laser spectroscopy beam into absorption spectroscopy measurement data. The reflector module comprises a reflective surface capable of reflecting the laser spectroscopy beam emitted by the laser emitter to the laser receiver. The transceiver and reflector modules are mountable on parts of the UAV such that the transceiver and reflector modules are spaced apart and the laser emitter and laser receiver have an unimpeded line of sight with the
(Continued)

reflecting surface. The electronics module is communicative with the transceiver module and with a flight computer of the UAV, and comprises a gas detection program that determines a concentration of the target gas from the measurement data received from the transceiver module; when the determined concentration of the target gas meets or exceeds an alarm threshold, the program records the received measurement data and instructs the flight computer to execute a defined flight plan for the UAV.

17 Claims, 7 Drawing Sheets

(51) Int. Cl.
*G01J 3/42* (2006.01)
*G01J 3/02* (2006.01)
G01N 21/3504 (2014.01)
G01N 21/17 (2006.01)

(52) U.S. Cl.
CPC .............. *G01N 2021/1795* (2013.01); *G01N 2021/3513* (2013.01); *G01N 2021/399* (2013.01); *G01N 2201/0214* (2013.01); *G01N 2201/0612* (2013.01)

(56) References Cited

U.S. PATENT DOCUMENTS

| | | |
|---|---|---|
| 2004/0263852 A1 | 12/2004 | Degtiarev et al. |
| 2012/0170024 A1* | 7/2012 | Azzazy ................ G01J 3/0202 356/51 |
| 2013/0292512 A1 | 11/2013 | Erben et al. |
| 2014/0204382 A1 | 7/2014 | Christensen |

OTHER PUBLICATIONS

Response to Written Opinion Amendment under Article 34 of the PCT, filed on Jun. 23, 2016, in International Application No. PCT/CA2015/050810.

International Preliminary Report on Patentability, dated Oct. 7, 2016, received in International Application No. PCT/CA2015/050810.

Extended European Search Report, dated May 14, 2018, received in European Patent Application No. 15 83 4894.

* cited by examiner

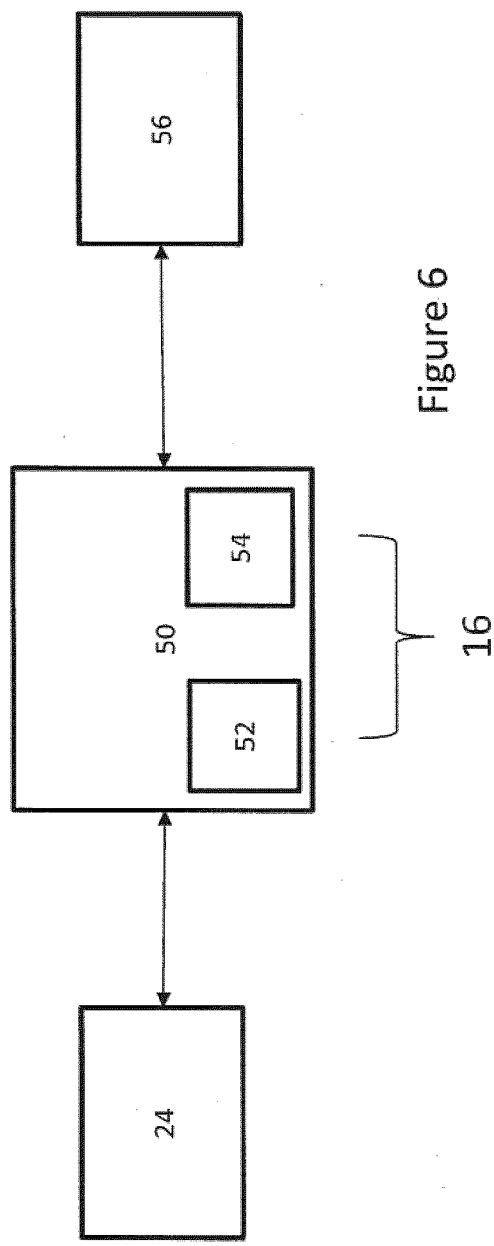

APPARATUS AND METHOD FOR DETECTING A GAS USING AN UNMANNED AERIAL VEHICLE

CROSS-REFERENCE TO RELATED APPLICATIONS

The present application is a U.S. National Stage entry under 35 U.S.C. § 371 of International Application No. PCT/CA2015/050810, filed on Aug. 24, 2015, designating the United States of America and published in English on Mar. 3, 2016, which in turn claims priority to U.S. Provisional Application No. 62/041,215, filed on Aug 25, 2014.

FIELD

This invention relates generally to an apparatus and a method for detecting a gas using an unmanned aerial vehicle ("UAV").

BACKGROUND

The Canadian Association of Petroleum Producers (CAPP) has established best practices for fugitive gaseous emissions measurement and management; however, cost-effective technologies for routine use in detecting and monitoring diffuse and point source leaks that percolate to the surface and into the atmosphere are relatively under-developed. While a number of emerging technologies are coming online, including differential absorption LiDARs, there are tradeoffs that pose challenges for operational use. For example, piloted aircraft can cover large areas and carry specialized sensors for detecting fugitive greenhouse gas ("GHG") sources; however, this method is very expensive and dangerous, and, therefore, unviable for routine monitoring. Ground-based "sniffer" or remote sensing methods, including in situ sensor networks, typically lack the spatial coverage to constrain diffuse sources, and in some settings they are impractical or cumbersome due to terrain conditions.

Therefore, it is desirable to provide a solution to overcome at least some of these challenges.

SUMMARY

According to one aspect of the invention, there is provided a gas detection apparatus mountable to an unmanned aerial vehicle (UAV) and which comprises a transceiver module, a reflector module or modules and an electronics module. The transceiver module comprises a laser emitter and a laser receiver; the laser emitter is tunable to emit a laser spectroscopy beam that can detect at least one target gas, and the laser receiver is configured to convert the laser spectroscopy beam into absorption spectroscopy measurement data. The reflector module(s) comprises one or more a reflective surface capable of reflecting the laser spectroscopy beam emitted by the laser emitter to the laser receiver. The transceiver and reflector modules are mountable on parts of the UAV such that the transceiver and reflector modules are spaced apart and the laser emitter and laser receiver have an unimpeded line of sight with the reflecting surface. The electronics module is communicative with the transceiver module and with a flight computer of the UAV, and comprises a gas detection program that determines a concentration of the target gas from the measurement data received from the transceiver module; when the determined concentration of the target gas meets or exceeds an alarm threshold, the program records the received measurement data and instructs the flight computer to execute a defined flight plan for the UAV.

The transceiver module can be mountable to a first winglet of the UAV and the reflector module can be mountable to a second winglet of the UAV opposite the first winglet. Alternatively, the gas detection apparatus can further comprise a pair of elongated members extending respectively from the transceiver module and the reflector module, which are attachable to the UAV such that the laser emitter and laser receiver have an unimpeded line of sight with the reflecting surface.

The transceiver module can further comprise a mount to which the laser emitter and laser receiver are mounted, and the reflector module can further comprise a mounting plate to which the reflecting surface is mounted. The mount and mounting plate can respectively comprise an elongated portion attachable to the UAV such that the laser emitter and laser receiver have an unimpeded line of sight with the reflecting surface.

The transceiver module can further comprise a reflector and the laser receiver can comprise an elongated fixture and a photodiode detector positioned on the fixture to correspond to a focal point of the reflector such that when the laser spectroscopy beam is received by the reflector it is reflected to the photodiode detector. The reflector can be an off-axis parabolic mirror.

The electronics module can be mountable in a fuselage of the UAV in which case the apparatus further comprises a fiber optic cable communicatively coupling the electronics module with the transceiver module.

The program code can further comprise a record leak subroutine comprising instructions to query the flight computer for current GPS coordinates of the UAV, associate the current GPS coordinates with current received measurement data, and then record current received measurement data with the associated current GPS coordinates.

The loopback flight plan can comprise a flight pattern that causes the UAV to fly in a loop from a location where the target gas was determined to have a concentration that exceeds the alarm threshold concentration. The program code can further comprise instructions to continuously receive measurement data from the transceiver module while the loopback flight plan is being executed. The program code can further comprise instructions to continuously record the received measurement data while the loopback flight plan is being executed.

According to another aspect of the invention, there is provided a method for detecting a gas using an unmanned aerial vehicle (UAV) comprising: flying the UAV along an initial flight plan; monitoring for a presence of the target using laser absorption spectroscopy and determining a concentration of the target gas when the presence of the target gas is detected; when the concentration of the target gas meets or exceeds an alarm threshold, and recording the determined target gas concentration and executing a loopback flight plan to cause the UAV to fly around a location where the target gas concentration was determined to meet or exceed the alarm threshold. The step of recording the determined target gas concentration can include querying a flight computer of the UAV for current GPS coordinates of the UAV, associating the current GPS coordinates with a current determined target gas concentration, and recording the current determined target gas concentration with the associated current GPS coordinates.

The method can further comprise receiving weather data for a region around the flight plan that includes wind speed and direction, and adjusting the loopback flight plan to compensate for movement of the target gas caused by wind.

BRIEF DESCRIPTION OF DRAWINGS

FIG. 6 is a block diagram of an electronics module of the gas detection apparatus communicatively coupled to the transceiver module and a flight computer of the UAV.

DETAILED DESCRIPTION

Figure 1:
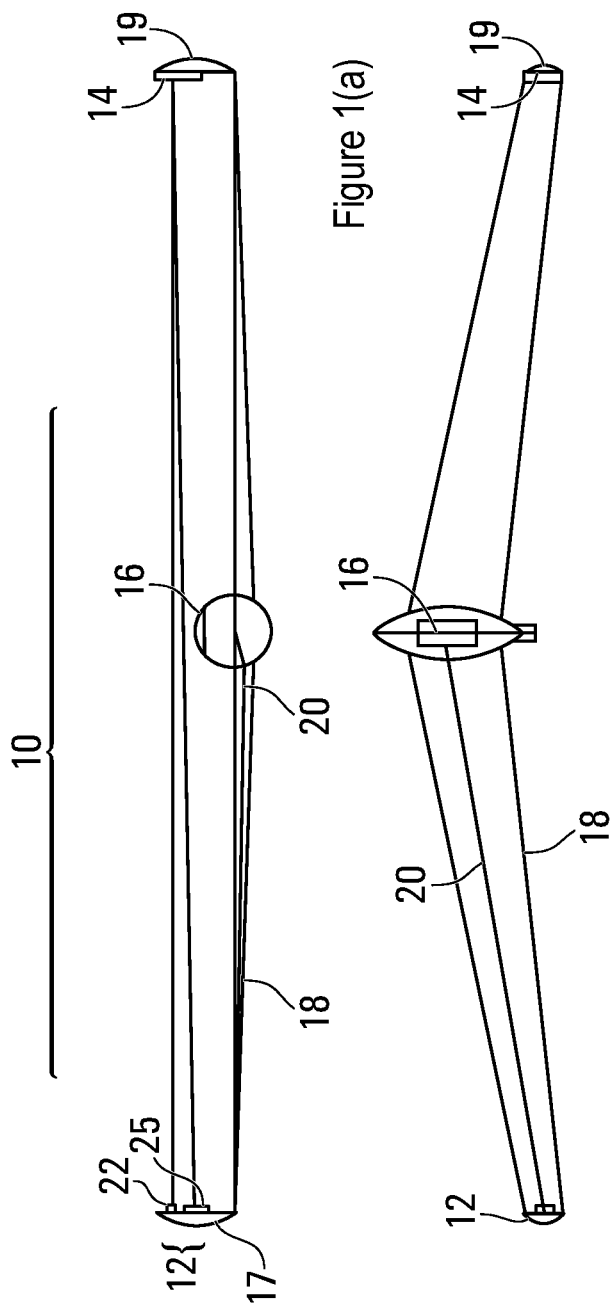
FIGS. 1(a) and (b) are respective rear elevation and top plan views of a gas detection apparatus mounted to a UAV, according to one embodiment of the invention.
Figure 2:
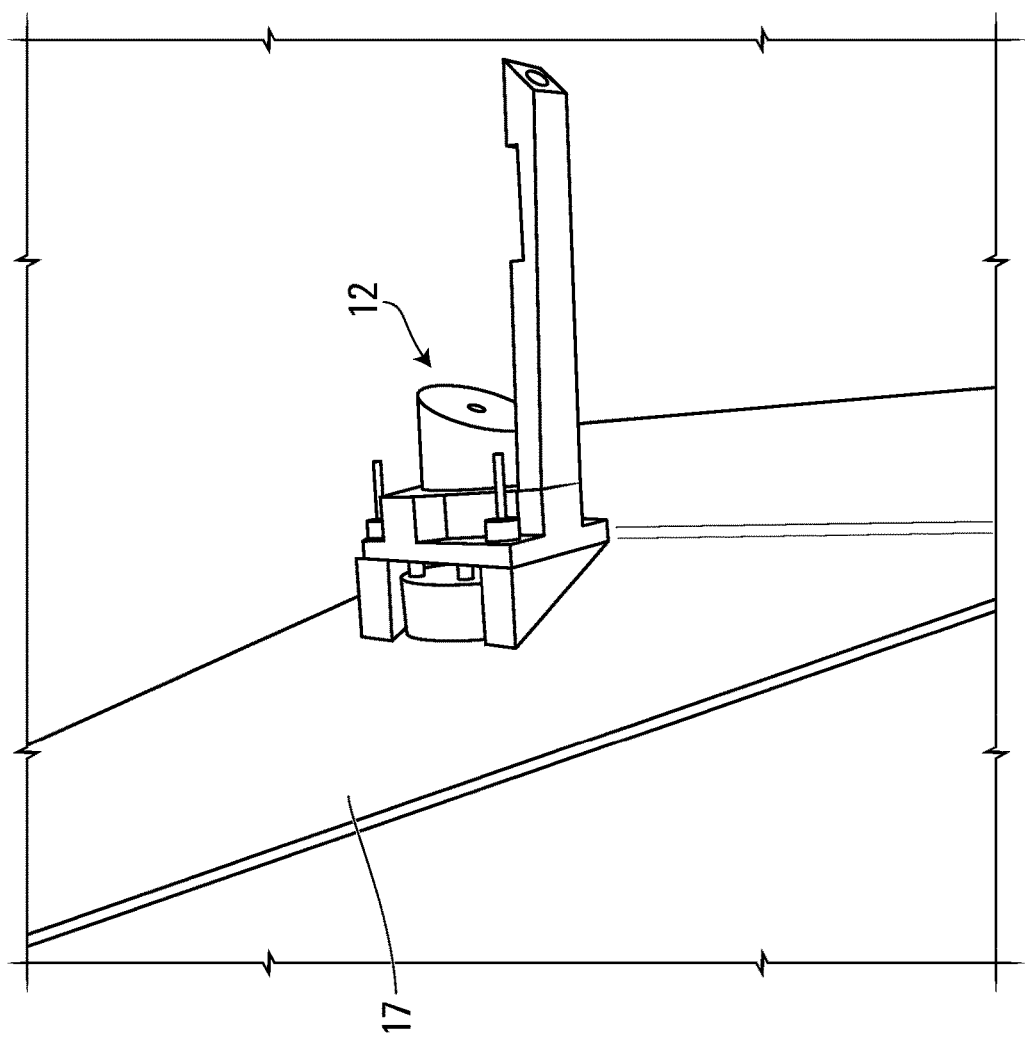
FIG. 2 is a detail perspective view of a transceiver module of the gas detection apparatus mounted to one winglet of the UAV.

Directional terms such as "upwards", "downwards", "horizontal", "vertical" and "lateral" are used in the following description for the purpose of providing relative reference only, and are not intended to suggest any limitations on how any apparatus is to be positioned during use, or to be mounted in an assembly or relative to an environment.

The embodiments described herein relate to an apparatus and a method for detecting gases such as $CO_2$ and $CH_4$ using a UAV. The UAV can be programmed to fly over a location of interest, i.e. a location where such gases are emitted, or leaks of such gases can occur, e.g. over a gas pipeline, natural areas, or an industrial facility. The apparatus comprises a transceiver module for transmitting and receiving a laser spectroscopy beam that is mounted on one winglet of the UAV, and a reflector module for reflecting the laser spectrometer beam that is mounted on the other winglet of the UAV. Together, the transceiver and reflector modules perform a laser-based absorption spectroscopy ("AS") method for detecting the concentration of certain target gases that pass through the laser spectroscopy beam.

The apparatus also comprises an electronics module that is communicative with the transceiver module; the electronics module includes a processor and a memory having stored thereon program code executable by the processor to read gas concentration measurement data collected by the transceiver module and when the measured gas concentration exceeds a defined alarm threshold, to continue measurement data recording and cause the UAV to execute a loopback flight plan around the location of the detected gases.

Referring now to FIGS. 1 to 8 and according to an embodiment of the invention, a gas detection apparatus 10 comprises a transceiver module 12, a reflector module 14, and an electronics module 16. The transceiver module 12 is mounted to a left winglet 17 of a UAV 18, the reflector module 14 is mounted to a right winglet 19 of the UAV 18, and the electronics module 16 is mounted in a fuselage of the UAV 18. The electronics module 16 is communicative with the transceiver module 12 via a fiber optic cable 20 and comprises a circuit board 50 with a processor 52 and a memory 54 containing program code for a gas detection program that is executable by the processor 52.

Figure 3A:
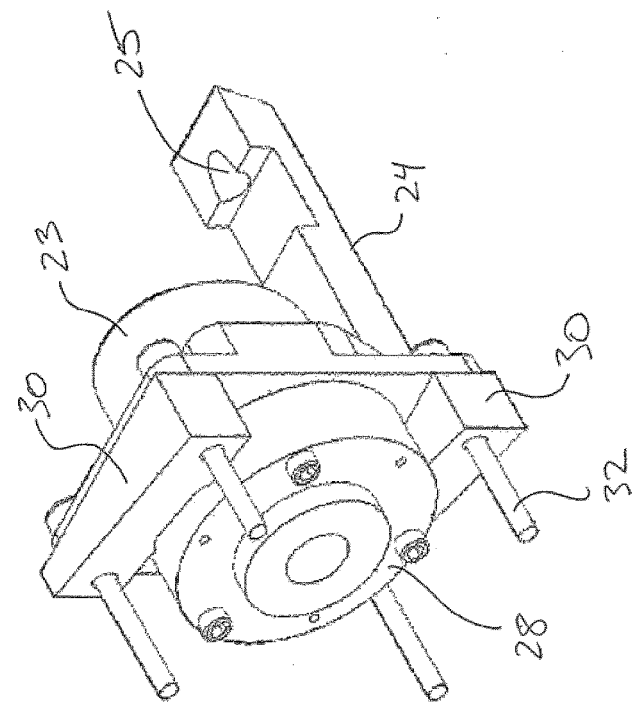
FIGS. 3(a) and 3(b) are front and rear perspective views of the transceiver module.
Figure 3B:
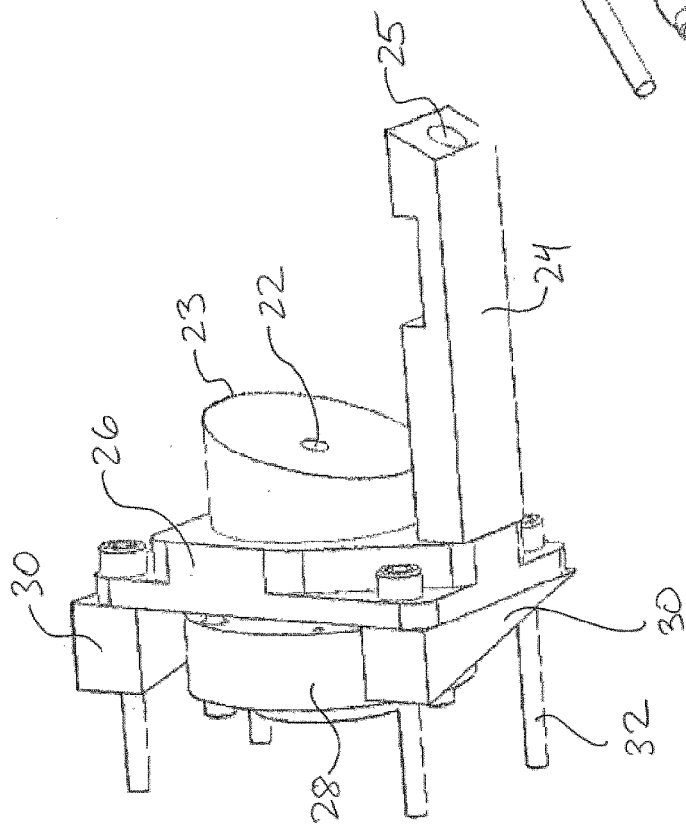

As can be seen more clearly in FIGS. 3(a) and (b), the transceiver module 12 comprises a laser emitter 22, a reflector 23 and a laser receiver 24 all mounted to a front side of a winglet mount 26. The reflector 23 in this embodiment is an off-axis parabolic (OAP) mirror, and the laser emitter 22 in this embodiment is a tunable diode laser emitter mounted in a hole in the center of the reflector 23. The laser receiver 24 comprises an elongated fixture extending from the mount 26, and a photodiode detector 25 attached to a distal end of the fixture; the position of the photodiode detector 25 is selected to correspond to the focal point of the reflector 23.

A fiber optic connector 28 is mounted to a rear side of the winglet mount 26 and allows the fiber optic cable 20 to couple to an output port of the laser receiver 24, thereby providing a communications link between the electronics module 16 and both of the laser emitter 22 and photodiode detector 25. A pair of wing shims 30 are attached to the rear side of the mount 26 and attach to an outer surface of the winglet 17; the shims 30 have shim angles which are selected to ensure that the laser emitter 22 and laser receiver 24 are aimed at the reflector module 14. The left winglet 17 is provided with holes for receiving the fiber optic connector 28 and four bolts 32 which extend from each corner of the winglet mount 26 and serve to physically attach the transceiver module 12 to the winglet 16. The fiber optic cable 20 runs from the fiber optic connector 28 inside the left wing of the UAV 18 to the electronics module 16.

Figure 5:
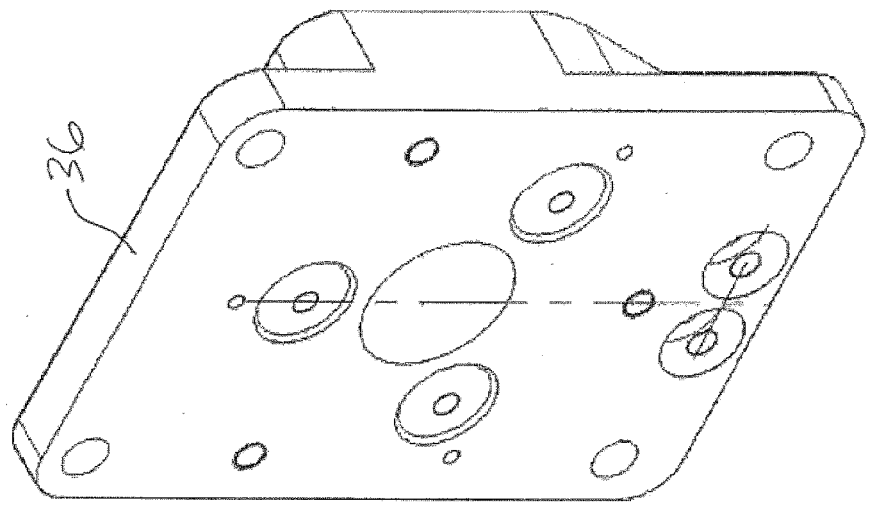
FIG. 5 is a perspective view of a winglet mounting plate of the reflector module.
Figure 4:
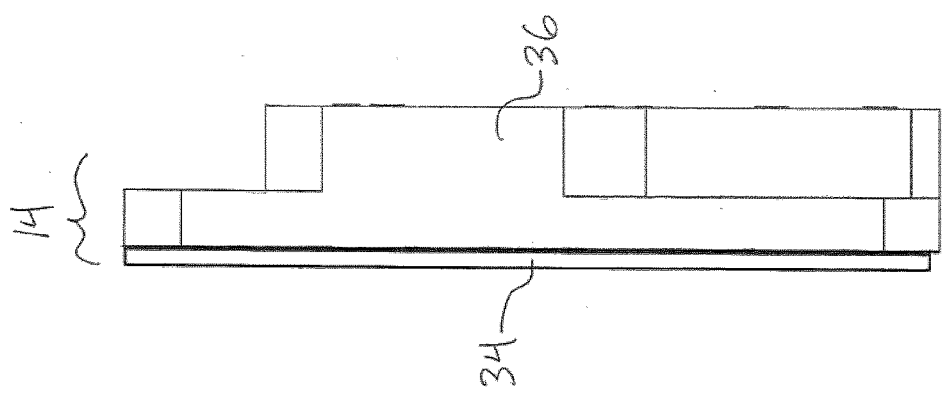
FIG. 4 is a side elevation view of a reflector module of the gas detection apparatus.

As can be seen more clearly in FIGS. 4 and 5, the reflector module 14 comprises a reflecting surface 34 and a winglet mounting plate 36 attached to the back of the reflecting surface 34. The reflector module 14 can also be provided with shims (not shown) to precisely align the reflecting surface 34 relative to the laser emitter 22 and receiver 24; alternatively, the back of the winglet mounting plate 36 can be configured to mount directly to the right winglet 19 such that the reflecting surface 34 is suitable aligned.

As can be seen in FIGS. 1(a) and (b), the transceiver and reflector modules 12 14 are positioned on the winglets 17, 19 above the fuselage such that there is a direct line of sight between the emitter 22/reflector 23 of the transceiver module 12 and the reflecting surface 34 of the reflector module 14. In this embodiment, the emitter 22 is configured to emit a single laser spectroscopy beam to the reflecting surface 34, which is then reflected once back to the reflector 23, which in turn reflects the beam to the photodiode detector 25. The frequency and other properties of the beam are selected based on the gas or gases that are desired to be detected. The process of detecting a gas by the laser beam is well known in the art and thus not discussed in detail here. In this embodiment, the gas detection apparatus 10 uses wavelength modulation spectroscopy ("WMS"), which is a form of absorption spectroscopy; however, other types of spectroscopic methods known in the art can alternatively be used.

According to an alternative embodiment (not shown), multiple reflectors can be provided (e.g. using multiple reflector modules 14) to extend the pathway of the laser spectroscopy beam pathway from the laser emitter 22 back to the laser receiver 24.

In this embodiment, the transceiver module 12 uses a tunable diode laser absorption spectroscopy method to detect certain target greenhouse gases like $CO_2$ and $CH_4$. The emission wavelength of the tunable diode laser emitter 25 is tuned over the characteristic absorption lines of the target gas. When the gas passes through the laser beam, there is reduction in the measured signal intensity by the photodiode detector 25; this measurement data is transmitted via the fiber optic cable 20 to the processor 52 in the electronics module 16, and program code stored on the memory 54 is executed which determines the gas concentration (and other properties) of the target gas from the measurement data (herein referred to as "Gas Concentration Determination subroutine"); when the determined gas concentration is below a defined alarm threshold (which for $CO_2$ and $CH_4$ can be at or around 0.5 ppm), the processor 52 sets an alarm bit register to 0; when the determined gas concentration is above the defined alarm threshold, the alarm bit register is set to 1. The selection and tuning of a suitable laser light source for the target gases and the algorithm used by the program code for determining a gas concentration from the photodiode detector measurements are known in the art and thus not described in detail here.

The UAV 16 can be any aircraft without an onboard human pilot, and in particular, can be controlled autonomously by an onboard computer or controlled remotely by a human or computer operator. Examples of suitable UAVs include fixed wing aircraft, quad-copters, multi-copters, balloons and blimps. As UAVs are well known in the art they are not described further in this description. In the present embodiment, the UAV 16 is a propeller-driven autonomously-controlled aircraft having a pair of wings with upwardly extending winglets that clear the height of the fuselage of the UAV 16. This UAV 16 is a relatively small unmanned aircraft system ("uUAS") having a light weight of about 3.8 Kg and capable of autonomous operation over an area of about 10 $km^2$. However, other types of UAVs can be used provided there is room to accommodate the gas detection apparatus modules 12, 14, 16 and there are winglets or other structures of the UAV which allow the transceiver and reflector modules 12, 14 to be mounted spaced apart from each other with an unimpeded line of sight. For example, the gas detection apparatus 10 can be mounted to the bottom of a quad-copter type UAV. If such winglets or other structures are not present on the UAV, then the gas detection apparatus 10 can further comprise a pair of laterally spaced elongated members (not shown) which can attach to the UAV such that an unimpeded line of sight can be established between the transceiver and reflector modules 12, 14. The elongated members can be separate parts, or respectively integrated into the transceiver and reflector modules 12, 14; for example the mount 26 and the mounting plate 36 can respectively comprise an elongated portion that allow the transceiver and reflector modules 12, 14 to attach to other parts of a UAV instead of the winglets. In another example, a long hanging tail (not shown) or an undercarriage (not shown) can be used to mount the transceiver and reflector modules 12, 14. Also, these structures can be adapted to mount multiple reflectors to elongate the pathway of the laser beam, in the manner as noted above.

Figure 7:
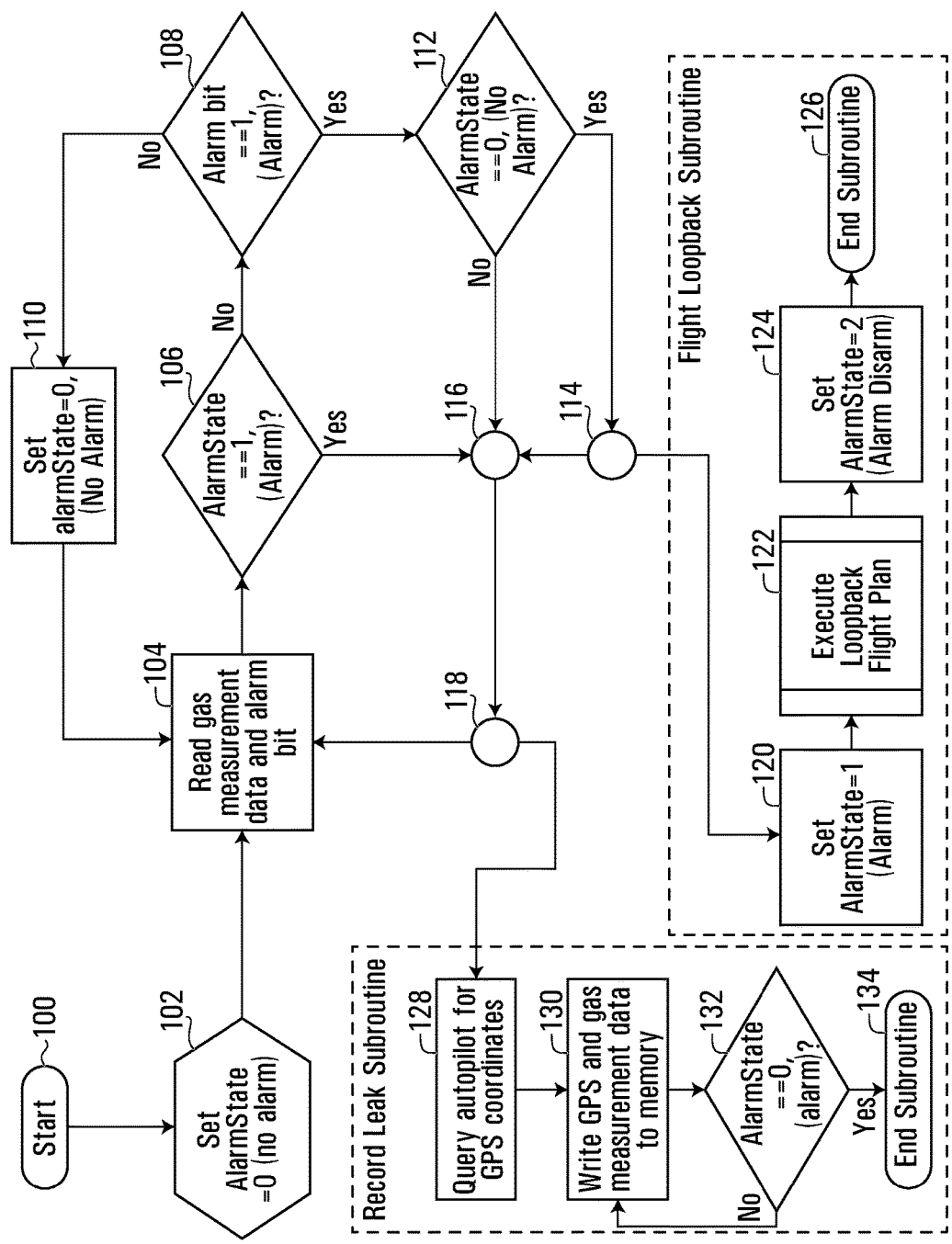
FIG. 7 is a logic diagram of a process carried out by the gas detection apparatus to execute a loopback flight plan and record gases when a gas leak is detected.

Referring now to FIG. 7, the gas detection program stored on the memory 54 is executable by the processor 52 to control the operation of the gas detection apparatus 10 and UAV 16 in response to measurement data received from the photodiode detector 25. As will be described in detail below, the gas detection program will cause the gas detection apparatus 10 to monitor and constantly record gas concentration when the measured concentration of the target gas is below the defined alarm threshold and to carry out a series of steps when the measured concentration of the target gas is at or above the defined alarm threshold. The target gas can be $CO_2$ or $CH_4$ in which case the minimum detection rate threshold can be 0.05 ppm. These steps include instructing the UAV 18 to execute a "Flight Loopback" subroutine wherein the UAV 18 flies around the location of the detected target gas according to a specific flight plan, while continuously recording the gas concentration measurement data. The Flight Loopback flight plan can be performed at multiple elevations and/or patterns to produce a large data point set that can be used later in a model to accurately determine the ground location of a gas leak.

The gas detection program comprises a controlled variable known as AlarmState that allows the gas detection apparatus 10 to be in one of three different states, namely, AlarmState=0 which indicates that there is no alarm state, AlarmState=1 which indicates that an alarm state should be initiated, and AlarmState=2 which indicates that the alarm state should be stopped. The gas detection program uses these AlarmStates along with the alarm bit number to determine when to execute and stop the Flight Loopback subroutines.

When the gas detection program is started, the AlarmState variable is set to 0 (step 102). The gas detection program then executes the Gas Concentration Determination subroutine to read the gas concentration measurement data and alarm bit register and determine the concentration of the target gas (step 104). When the AlarmState is 0 and the alarm bit is 0, the target gas concentration is below the alarm threshold and the gas detection program remains in a "no alarm" state and continues to execute the Gas Concentration Determination subroutine, i.e. continues to read the gas concentration measurement data and the alarm bit register (steps 106, 108 and 110). This subroutine will run repeatedly until the gas detection apparatus 10 is shut down, or the measured concentration of the target gas meets or exceeds the alarm threshold concentration.

When the alarm threshold concentration is met or exceeded, the Gas Concentration Determination subroutine will set the alarm bit register to 1, and the gas detection program will then check whether the AlarmState is still 0 (step 112). As nothing has caused the AlarmState to change yet, AlarmState will still be 0 and thus the program moves to steps 114, 116, and 118 which cause the Flight Loopback and Gas Concentration Determination subroutines to be executed simultaneously.

The Flight Loopback subroutine comprises first initiating an alarm state by setting the AlarmState to 1 (step 120), then executing a loopback flight plan (step 122). The loopback flight plan comprises instructions sent by the gas detection apparatus 10 to a flight computer of the UAV 16, to cause the UAV 16 to execute a "loopback" flight plan comprising a predefined flight pattern around the location where the target gas was first detected to exceed the alarm threshold concentration. The loopback flight plan can be stored on the memory 54 of the gas control apparatus 10, and be sent along with the instructions to the UAV flight computer, or, the loopback flight plan can be stored on a memory of the UAV flight computer, in which case, only instructions to execute the flight pattern are sent by the gas control apparatus 10 to the UAV flight computer.

Figure 8:
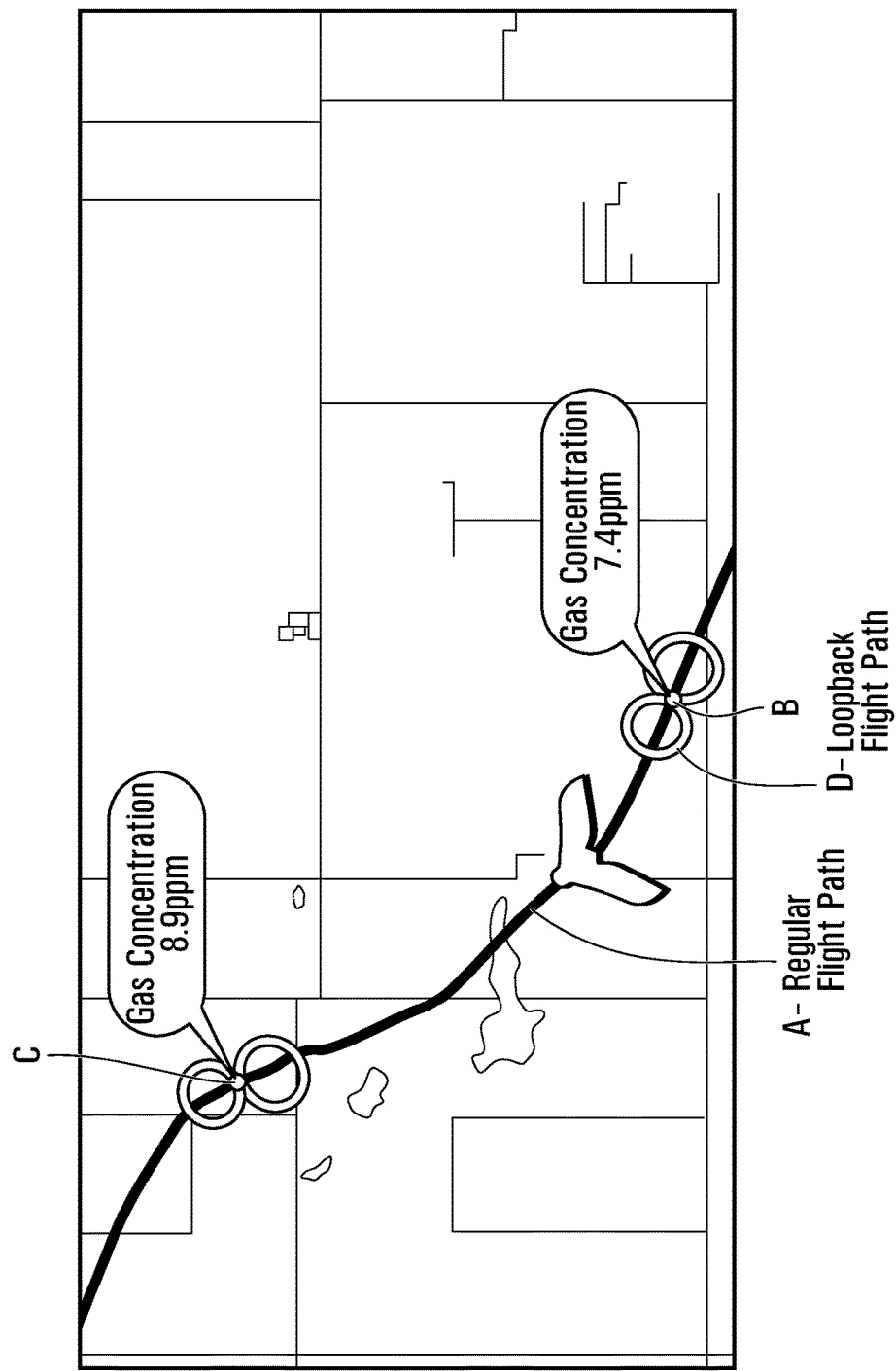
FIG. 8 is a plan view of the loopback flight plan executed by the UAV when a gas leak is detected.

An exemplary flight pattern for the loopback flight plan is shown in FIG. 8. In this Figure, the UAV flies along a predefined flight plan comprising a series of waypoints along a pipeline A ("regular flight path"), and monitors gas concentration per step 104 of the gas detection program. At location B, the UAV 16 detects a target gas concentration of 7.4 ppm which is a gas event that exceeds the alarm threshold and causes the gas detection program to initiate the Flight Loopback subroutine to cause the UAV 16 to execute the loopback flight plan comprising circling in a FIG. 8 loop configuration (shown as "D" in FIG. 8), of about 40-80 meters. Each time the UAV 16 completes one FIG. 8 loop it flies a set distance then returns back to location B to fly through the gas event again. This is repeated three times. The flight pattern can be at multiple elevations to get more data points for modelling after the flight. Once the Flight Loopback subroutine has completed, the processor 52 terminates the alarm state by setting AlarmState to 2, and ends the Flight Loopback subroutine. Alternatively, the loopback flight plan can have different configurations, such as a circular loop.

While the Flight Loopback subroutine is being executed, the processor 52 also executes the Gas Concentration Determination subroutine again, as the gas detection program returns to step 104 via steps 114, 116 and 118. Since the AlarmState is now 1, the gas detection program will repeatedly read and record the gas concentration measurement data and alarm bit register (i.e. loop between steps 104, 106, 116 and 118) until the loopback flight plan is completed and the alarm state is terminated (i.e. once the AlarmState is set to 2 in the Flight Loopback subroutine). If the measured gas concentration level has fallen below the alarm threshold when the loopback flight plan has completed (and the UAV returns back to its original flight plan), the alarm bit register will be set to 0, and the gas detection program will return to a no alarm state (set AlarmState to 0, step 110) and continue monitoring gas concentration levels with continuous recording (step 104). If instead the measured gas concentration level remains at or above the alarm threshold, the alarm bit register will be set to 1, and the gas detection program will set the alarm to a null state until the UAV travels a defined distance from the last known gas location (location A in FIG. 8) to clear the gas sensing equipment (in transceiver 12); after this distance has been travelled, the gas detection program returns back to the original AlarmState of 0 and starts monitoring gas concentration again. In the example shown in FIG. 8, the gas detection program returns the UAV back to its original flight plan. The UAV encounters another gas event at location C, and the gas detection program initiates another Flight Loopback subroutine at this location.

A Record Leak subroutine is executed at the same time as the Flight Loopback and Gas Concentration Determination subroutines when the AlarmState is 0 and the alarm bit register is 1 or at the same time with just the Gas Concentration Determination subroutine when the AlarmState is 2 and the alarm bit is 1. In both cases, the Record Leak subroutine comprises causing the processor 52 to query the UAV flight computer for the current GPS coordinates of the UAV 16 (step 128), then receive the GPS coordinates and the gas concentration measurement data at those coordinates and record both to the memory 54 (step 130). The subroutine then checks whether the AlarmState is 0 (step 132) and if yes, (e.g. after the Flight Loopback subroutine has completed and the Gas Concentration Detection subroutine reads the alarm bit register to be 0 and then sets the AlarmState to 0), the subroutine will end (step 134). If AlarmState is not 0 (e.g. after the Flight Loopback subroutine has completed with the AlarmState set to 2 and the Gas Concentration Detection subroutine reads the alarm bit register to be 1) the subroutine continues to write the gas concentration measurement data and the associated GPS coordinates to memory.

The gas detection program can be programmed to adjust the altitude of the UAV 16 during its flight path; for example, the gas detection program can cause the UAV 16 to rise up 50 m or descend 5-25 m to more accurately model a gas event. Also, the loopback flight plan can have different flight patterns; for example, an alternative flight pattern comprises executing at least one clockwise loop and at least one counter-clockwise loop from the detected gas event location. Such a flight pattern may be particularly useful to get a better sense of wind direction and target gas movement. Also, the get detection program can be further programmed to record wind speed and vector along with the gas concentration level and other data.

The gas detection program can be further programmed to adjust the flight pattern of the UAV using data from the UAV's flight speed and pressure sensing pilot tube (not shown), which may result in better detection of a gas plume. In particular, UAV 16 can use weather data from ground bases along with its in-flight pressure, altitude and wind speed sensor (not shown) to adjust the flight path to better position the unit to fly through the center of the gas plume, especially in cases where wind will cause the gas plume to shift over the course of the UAV's flight path. The gas detection program will receive weather data for a region around the UAV flight plan that includes wind speed and direction, and adjust the loopback flight plan to compensate for movement of the target gas caused by wind. For example, if the UAV 16 is flying south to north at a 60 m elevation and the wind is coming out of the west going east @ 90 deg, the gas detection program can be programmed to shift the UAV's flight path over to the east 10-50 m to center on the gas plume being push over by the wind.

The scope of the claims should not be limited by the preferred embodiments set forth in the examples, but should be given the broadest interpretation consistent with the description as a whole.

The invention claimed is:

1. A gas detection apparatus comprising:
   (a) a transceiver module comprising a laser emitter and a laser receiver, wherein the laser emitter is tunable to emit a laser spectroscopy beam that can detect at least one target gas, and the laser receiver is configured to convert the laser spectroscopy beam into absorption spectroscopy measurement data;
   (b) at least one reflector module comprising a reflective surface capable of reflecting the laser spectroscopy beam emitted by the laser emitter to the laser receiver; and
   (c) an electronics module communicative with the transceiver module and with a flight computer of an unmanned aerial vehicle ("UAV"), and comprising a processor and a memory having stored thereon program code executable by the processor to determine a concentration of the target gas from the measurement data received from the transceiver module, and when the determined concentration of the target gas meets or exceeds an alarm threshold, to record the received measurement data and instruct the flight computer to execute a loopback flight plan for the UAV;
   wherein the transceiver and reflector modules are mountable on parts of the UAV such that the transceiver and reflector modules are spaced apart and the laser emitter and laser receiver have an unimpeded line of sight with the reflecting surface.

2. An apparatus as claimed in claim 1 wherein the transceiver module is mountable to a first winglet of the UAV and the reflector module is mountable to a second winglet of the UAV opposite the first winglet.

3. An apparatus as claimed in claim 1 wherein the gas detection apparatus further comprises a pair of elongated members extending respectively from the transceiver module and the reflector module and attachable to the UAV such that the laser emitter and laser receiver have an unimpeded line of sight with the reflecting surface.

4. An apparatus as claimed in claim 1 wherein the transceiver module further comprises a mount to which the laser emitter and laser receiver are mounted, and the reflector module further comprises a mounting plate to which the reflecting surface is mounted, the mount and mounting plate respectively comprising an elongated portion attachable to the UAV such that the laser emitter and laser receiver have an unimpeded line of sight with the reflecting surface.

5. An apparatus as claimed in claim 2 wherein the transceiver module further comprises a reflector and the laser receiver comprises an elongated fixture and a photodiode detector positioned on the fixture to correspond to a focal point of the reflector such that when the laser spectroscopy beam is received by the reflector it is reflected to the photodiode detector.

6. An apparatus as claimed in claim 3 wherein the reflector is an off-axis parabolic mirror.

7. An apparatus as claimed in claim 2 wherein the electronics module is mountable in a fuselage of the UAV and the apparatus further comprises a fiber optic cable communicatively coupling the electronics module with the transceiver module.

8. An apparatus as claimed in claim 1 wherein the program code further comprises a record leak subroutine comprising instructions to query the flight computer for current GPS coordinates of the UAV, associate the current GPS coordinates with current received measurement data, and then record current received measurement data with the associated current GPS coordinates.

9. An apparatus as claimed in claim 1 wherein the loopback flight plan comprises a flight pattern that causes the UAV to fly in multiple loops from a location where the target gas was determined to have a concentration that exceeds the alarm threshold concentration.

10. An apparatus as claimed in claim 9 wherein the program code further comprises instructions to continuously receive measurement data from the transceiver module while the loopback flight plan is being executed.

11. An apparatus as claimed in claim 9 wherein the program code further comprises instructions to continuously record the received measurement data while the loopback flight plan is being executed.

12. An apparatus as claimed in claim 1 further comprising multiple reflector modules each positioned to reflect the laser spectroscopy beam in a continuous pathway from the laser emitter to the laser receiver.

13. A method for detecting a gas using an unmanned aerial vehicle (UAV) comprising:
    (a) flying the UAV along an initial flight plan;
    (b) monitoring for a presence of the target using laser absorption spectroscopy and determining a concentration of the target gas when the presence of the target gas is detected, wherein the target gas is detected in a space between a laser transceiver module and a laser reflector module mounted to the UAV, and wherein a laser spectroscopy beam that can detect the target gas is emitted from the laser transceiver module, reflected by the laser reflector module and received by the laser transceiver module;
    (c) when the concentration of the target gas meets or exceeds an alarm threshold, recording the determined target gas concentration and executing a loopback flight plan to cause the UAV to fly around a location where the target gas concentration was determined to meet or exceed the alarm threshold.

14. A method as claimed in claim 13 wherein the step of recording the determined target gas concentration includes querying a flight computer of the UAV for current GPS coordinates of the UAV, associating the current GPS coordinates with a current determined target gas concentration, and recording the current determined target gas concentration with the associated current GPS coordinates.

15. A method as claimed in claim 14 further comprising continuously monitoring for the presence of the target gas while the loopback flight plan is being executed.

16. A method as claimed in claim 14 further comprising continuously recording the current determined target gas concentration with the associated current GPS coordinates while the loopback flight plan is being executed.

17. A method as claimed in claim 13 further comprising receiving weather data for a region around the flight plan that includes wind speed and direction, and adjusting the loopback flight plan to compensate for movement of the target gas caused by wind.

* * * * *